United States Patent [19]

Kresh et al.

[11] Patent Number: 4,936,304
[45] Date of Patent: Jun. 26, 1990

[54] PACING SYSTEM AND METHOD FOR CARDIAC PACING AS A FUNCTION OF DETERMINED MYOCARDIAL CONTRACTILITY

[75] Inventors: J. Yasha Kresh, Philadelphia; Stanley K. Brockman, Narberth, both of Pa.

[73] Assignee: Thomas Jefferson University, Philadelphia, Pa.

[21] Appl. No.: 133,261

[22] Filed: Dec. 16, 1987

Related U.S. Application Data

[63] Continuation of Ser. No. 785,138, Oct. 7, 1985, abandoned.

[51] Int. Cl.$^5$ .............................................. A61N 1/36
[52] U.S. Cl. .............................................. 128/419 PG
[58] Field of Search ................................. 128/784–786, 128/673

[56] References Cited

U.S. PATENT DOCUMENTS

| | | | |
|---|---|---|---|
| 3,857,399 | 12/1974 | Zacuoto | 128/419 P |
| 4,026,303 | 5/1977 | Babotai | 128/419 P |
| 4,052,991 | 10/1977 | Zacouto | 128/419 PG |
| 4,424,812 | 1/1984 | Lesnick | 128/419 PG |
| 4,535,774 | 8/1985 | Olson | 128/419 |
| 4,543,954 | 10/1985 | Cook et al. | 128/419 PG |
| 4,600,017 | 7/1986 | Schroeppel | 128/419 P |
| 4,791,931 | 12/1988 | Slate | 128/419 PG |

FOREIGN PATENT DOCUMENTS 0080347 11/1982 European Pat. Off. .
0178528 4/1986 European Pat. Off. .

OTHER PUBLICATIONS

IEEE Engineering in Medicine and Biology Magazine, Jun. 1984 pp. 25–29 and Table of Contents page.
Gaeltee Catheter Transducers Specifications 2 pages ©1980.
Millar Instruments Inc, Micro-Tip ® Pressure Sensor Specifications, 4/5/83.

Primary Examiner—Francis Jaworski
Attorney, Agent, or Firm—Ladas & Parry

[57] ABSTRACT

A cardiac pacing system and method provides rate control as a function of sensed myocardial contractility. A signal representative of short term, e.g. cycle-to-cycle, heart contractility is derived from a sensor which measures intramyocardial pressure. A microprocessor-band controller provides logic and memory capacity for carrying out a signal processing algorithm for determining and selecting optimum pacing rate as a function of sensed intensity of the active state of the cardiac muscle.

30 Claims, 6 Drawing Sheets

PACING SYSTEM AND METHOD FOR CARDIAC PACING AS A FUNCTION OF DETERMINED MYOCARDIAL CONTRACTILITY

This is a continuation of application Ser. No. 785,138, filed Oct. 7, 1985, now abandoned.

BACKGROUND OF THE INVENTION

This invention relates to demand-type pacing systems and methods and, more particularly, to rate-adaptive pacing systems and methods for controlling cardiac pacing rate as a function of a monitored cardiac parameter such as myocardial viability.

Rate adaptive pacemaker systems are known in the art and are receiving increasing attention and commercialization. Historically, the first rate adaptive pacing systems have been the dual chamber systems, e.g. atrial synchronous systems, where the pacing of the ventricle is coupled to or synchronized with detected atrial beats. Such dual chamber systems have the clear advantage of optimally simulating normal physiological response, since they derive the timing of the pacing pulses from the atrial response which is induced by the natural heart pacemaker. However, dual chamber systems have certain disadvantages which have been recognized in the literature, as well as certain practical disadvantages. It has been reported that atrial synchronous pacing is not suitable for up to 76% of pacemaker-indicated patients. See Rate Responsive Pacing, Rickards et al, Clin. Prog. Pacing and Electrophysiology, Vol. 1, No. 1, 1983, pp. 12-18.

Dual chamber pacemakers have never been prescribed with the frequency of single chamber pacemakers, for the practical reasons of expense, the need to place pacing leads into both chambers and the potential complexities of dual chamber pacing (such as pacemaker mediated tachycardia) which can be avoided in patients who can be well treated with the simpler single chamber systems.

The single chamber demand pacemaker, while simplest and most reliable in terms of system complexity, carries the fundamental limitation of not being able to adapt its response to normal patient needs. It is well known that the requirements of blood flow vary widely as a function of both physiological (exercise) and emotional occurrences. The normal heart adjusts blood flow by varying both stroke volume and rate, the blood flow being the result of the product of those two variables. While a single chamber pacemaker cannot adjust stroke volume, it can adjust heart rate by the relatively simple technical expedient of adjusting the rate of the delivered pulses. The adjustment of rate alone is considered to provide about 80% of the total blood flow change. See the above-cited Rickards et al paper.

In response to the recognized desirability of being able to automatically adapt pacing rate, e.g., increase exercise tolerance, there has been a great deal of work and progress, including several commercial pacemakers incorporating different feedback systems for controlling pacing rate as a function of one or more sensed cardiac or body parameters. For a summary of such systems, see "Principles of Exercise-Responsive Pacemakers," IEEE Engineering in Medicine and Biology Magazine, Jun. 1984, pp. 25-29; "The Exercise-Responsive Cardiac Pacemaker," IEEE Transaction on Biomedical Engineering, Vol. BME 31, No. 12, Dec. 1984.

The system and method of this invention are based upon our observation that the rate adaptive pacemaker principle is efficiently carried out by controlling the function of one or more parameters which normally and directly control (or are concomitant with) pacing rate in a healthy person. This approach is contrasted to many of the systems that are presently being investigated, wherein indirect parameters such as respiration rate, oxygen saturation, etc. are monitored and utilized in the rate adaptive feedback loop. It is known that there are a number of pathways that directly affect the heart, one being the cardiac sympathetic nerves, and the other being direct release of hormones or catecholamines into the bloodstream. In a normal state the neuroendocrine system stimulates various cardiovascular receptor sites, thus controlling both the heart rate, which is triggered by the natural pacemaker (sinus node) and myocardial contractility which brings about an increase in hemodynamics (pressure-flow). In patients who do not have an intact conduction system, e.g., sino-atrial node dysfunction, the concomitant events that should take place, namely increase in rate and contractility, are disrupted or impaired. Thus we make our observation that the ability to directly detect changes in sympathetic drive, ventricular contractility or circulation catecholamine levels constitute an appropriate means of obtaining information for control of a pacemaker.

It is very unlikely that an artificial chemoreceptor for detecting sympathetic tone or catecholamine level can be perfected in the near future, although such an accomplishment could provide a medically attractively solution to pacemaker control. Another more practical approach for the present in achieving a closed-loop physiologically responsive pacing system is to measure changes in the contractile state of the cardiac muscle itself. This can be accomplished, at least presently, by two different means. A first means is to measure stress in the muscle wall (intramyocardial pressure, or IMP) and the other is to measure the regional wall thickening or fiber-shortening of the muscle. The former can be done by use of ultrasonic A-scan imaging, and the latter with sonomicrometers which are implantable ultrasonic crystals used to measure changes in the relative motion of a given myocardial region. The more feasible approach in terms of practical implementation is the measurement of intramyocardial stress or pressure. The preferred embodiments of our invention, as set forth herein below, utilize the IMP approach.

SUMMARY OF THE INVENTION

It is an object of this invention to provide an improved rate responsive single chamber pacemaker, and method of pacing.

It is another object of this invention to provide a pacing system and method which optimally adjusts pacing rate as a function of a physiological parameter which directly affects normal cardiac output, e.g., myocardial contractility.

It is another object of this invention to provide a rate responsive pacing system and method wherein one or more parameter sensors is utilized on the same lead which delivers pacing signals and senses patient heartbeats.

In accordance with the above objects, there is disclosed a demand pacing system which constitutes an improvement on conventional demand pacing systems by providing rate control as a function of sensed myocardial contractility. The apparatus of this system preferably utilizes a microprocessor-based controller. The controller provides logic means and memory capacity for carrying out a signal processing algorithm for determining and selecting optimum pacing rate as a function of sensed myocardial contractility, independent of atrial activity. In addition, a threshold seeking algorithm is incorporated to avoid false triggering. In the preferred embodiment a sensor is used which generates a signal representative of intramyocardial pressure, and pacing rate is varied directly as a function of the sensed IMP signal characteristics. The high sensitivity of the sensor provides system reliability, and an overall system response of less than 30 seconds is achieved.

A DESCRIPTION OF THE PREFERRED EMBODIMENTS

Figure 1A:
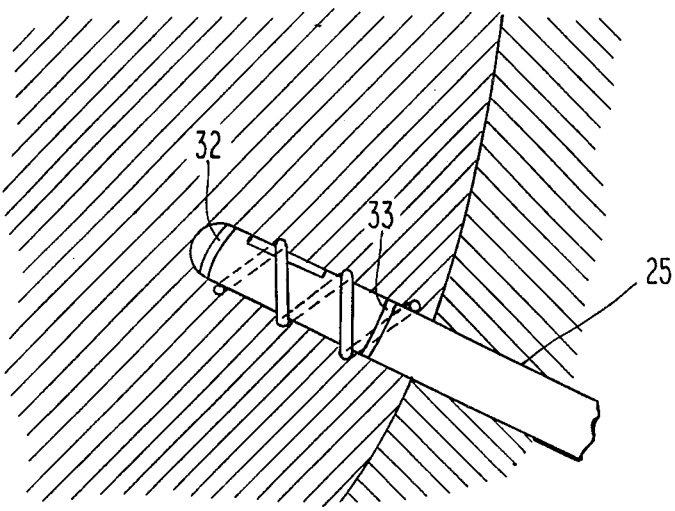
FIG. 1A is a schematic illustration of a lead tip placed in the myocardium of the left ventricle, the lead tip containing an IMP sensor as well as pacing electrodes.
Figure 1B:
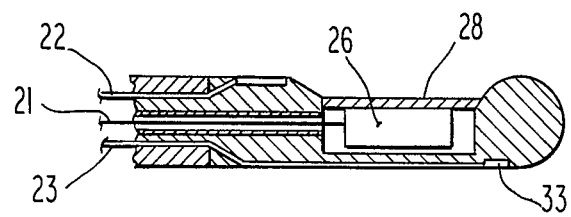
FIGS. 1B and 1C are schematic illustrations of an electrode tip of this invention showing a pressure sensor and electrodes.
Figure 1C:
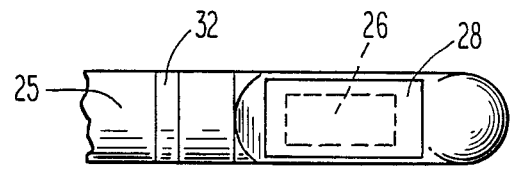

As discussed above, and illustrated in the drawings, this invention comprises a pacemaker system and method for controlling pacing rate as a function of sensed myocardial contractility. Although other types of sensors can be used within the scope of this invention, the preferred embodiments are illustrated utilizing a pressure sensor for sensing of IMP. Referring to FIG. 1A, there is shown a schematic of a sensor adapted to be placed in the myocardium of the left ventricle. The sensor preferably has threads—enabling it to be screwed into the myocardium. The sensor 26 is positioned on the tip of lead 25, which lead also carries electrodes 32, 33. The pressure sensor and electrodes are connected by suitable conductors, not shown, to the pacemaker of the system. As seen in FIGS. 1B and 1C, the pressure sensor is implanted within the tip of the lead, and may be covered by a silicone rubber diaphragm 28 or other suitable cover which permits the external pressure to be communicated through to the sensor. The sensor is shown communicating through the lead by means of one or more conductors 21. The electrodes 32, 33, communicate electrically through the lead by conductors 22, 23. As is well known, the pacing system may be unipolar or bipolar, this being a matter of design choice.

A preferred sensor for assessing IMP is a MIKROTIP (registered trademark) pressure sensor made by Melar Instruments, or an MMI-Gaeltec transducer. The pressure sensor is preferably mounted at the end of a 3-Fr catheter, being 1 mm in diameter. The transducer operates on the principle of producing a varying electrical signal output proportional to the magnitude of sensed pressure stress resulting from deformation or strain of a difused semi-conductor. Conventional electronics (full-bridge circuit) converts this resistance change to voltage change indicative of stress or pressure applied directly on the sensing area.

Figure 1D:
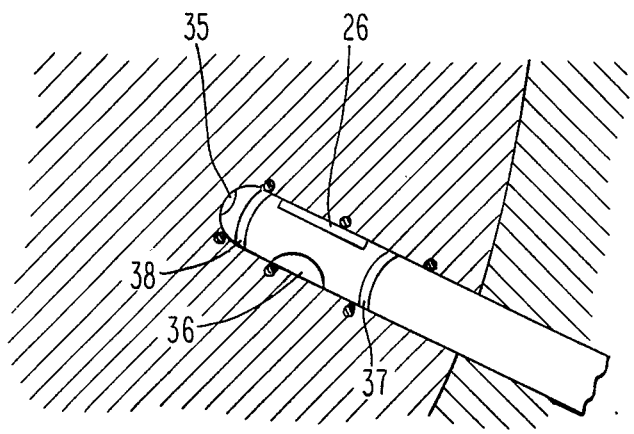
FIG. 1D is a schematic illustration of an alternate electrode tip placed in the myocardium.

FIG. 1D is another schematic view of a catheter or lead tip for use in this invention, which includes one or more additional sensors as well as the IMP sensor. A thermistor 35 is illustrated at the very end of the tip, and a pH sensor is also illustrated at 36. Appropriate leads through the catheter length are utilized for communicating the sensor signals back to the pacemaker. As discussed hereinbelow, the utilization of additional sensed parameters is embraced within an embodiment of this invention, the additional information being utilized to correlate the IMP data in determining the desired pacing rate. Also, as mentioned above, although not illustrated, additional types of mycardial contraction sensors are available and are within the scope of this invention, i.e. ultrasonic A-scan imaging and intramural sonomicrometric sensors.

Figure 2A:
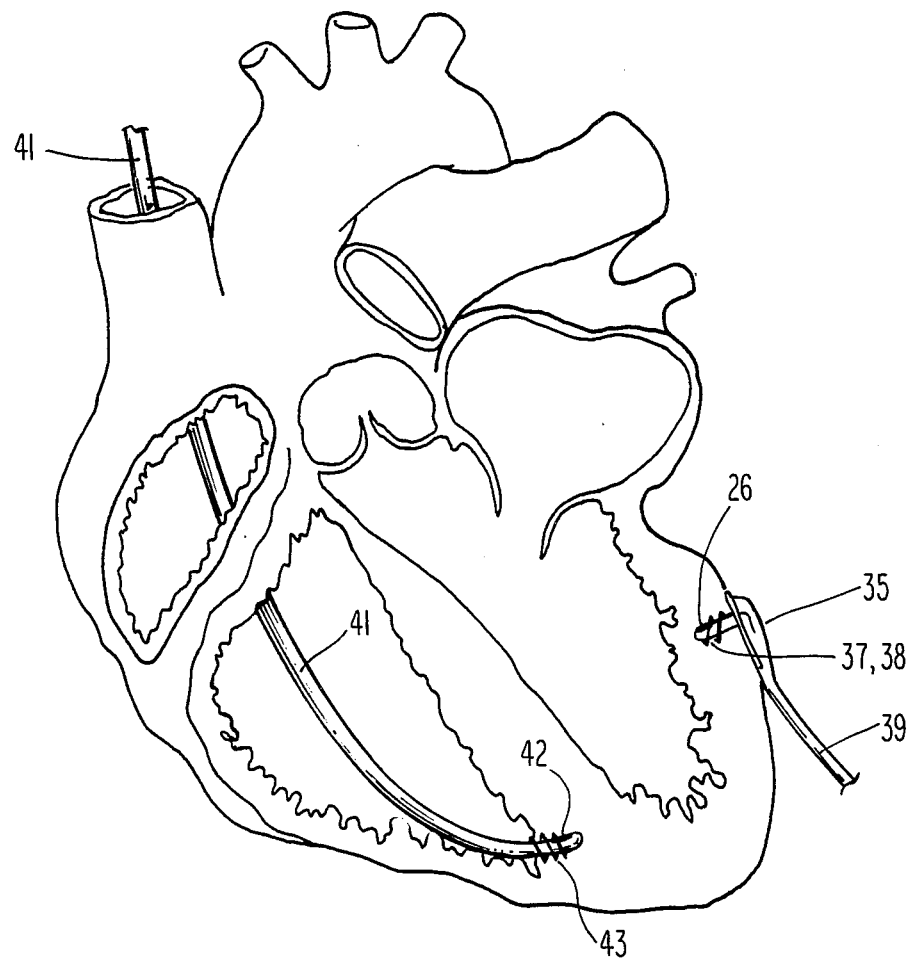
FIG. 2A is a schematic illustration showing a screw in tip in accordance with this invention placed in the myocardium of the left ventricle, and a transvenous catheter with another tip in accordance with this invention positioned in the myocardium at the septum or apex of the right ventricle.
Figure 2B:
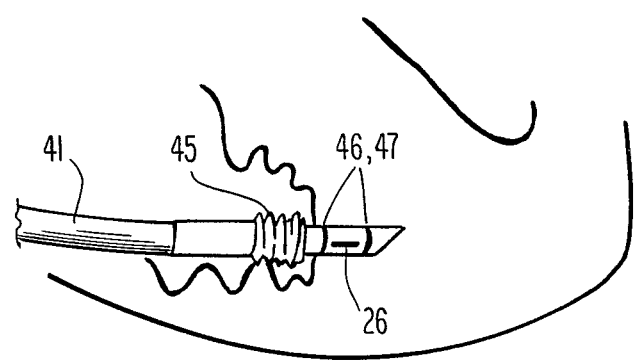
FIG. 2B is an enlarged schematic showing the detail of the tip of the transvenous catheter illustrated in FIG. 2A.

Referring now to FIG. 2A, there is shown a representation of a human heart with two illustrations of lead placements as may be utilized in the practice of this invention. A screw-in epicardial-type lead 39 having a tip head 35 is shown screwed into the heart wall, penetrating through the epicardium into the myocardium of the left ventricle. The technique that is used with this type of electrode is the known technique of securing the electrode to the heart wall through a left thoracotomy. An alternate embodiment uses a conventional transvenous catheter, or lead system as illustrated by lead 41, having the pressure sensor located as indicated at 42 at the distal tip end, and having fixation means 43. It is known in the art that transvenous electrodes are available for insertion into the right ventricle, with varying types of fixation elements for fixing the lead against and indeed into the heart wall. As indicated in FIG. 2B, the transvenous electrode lead 41 may have a retractable sleeve 45 operable in a known fashion for exposing the far distant tip of the lead after initial placement within the right ventricle. For placement in the right ventricle, it is noted that the right ventricle wall is relatively thin and thus not preferable for providing a good indication for wall stress changes resulting from changing contractility. It is accordingly necessary to position or steer the lead so that it is anchored in the apex, or the septal wall.

Figure 3:
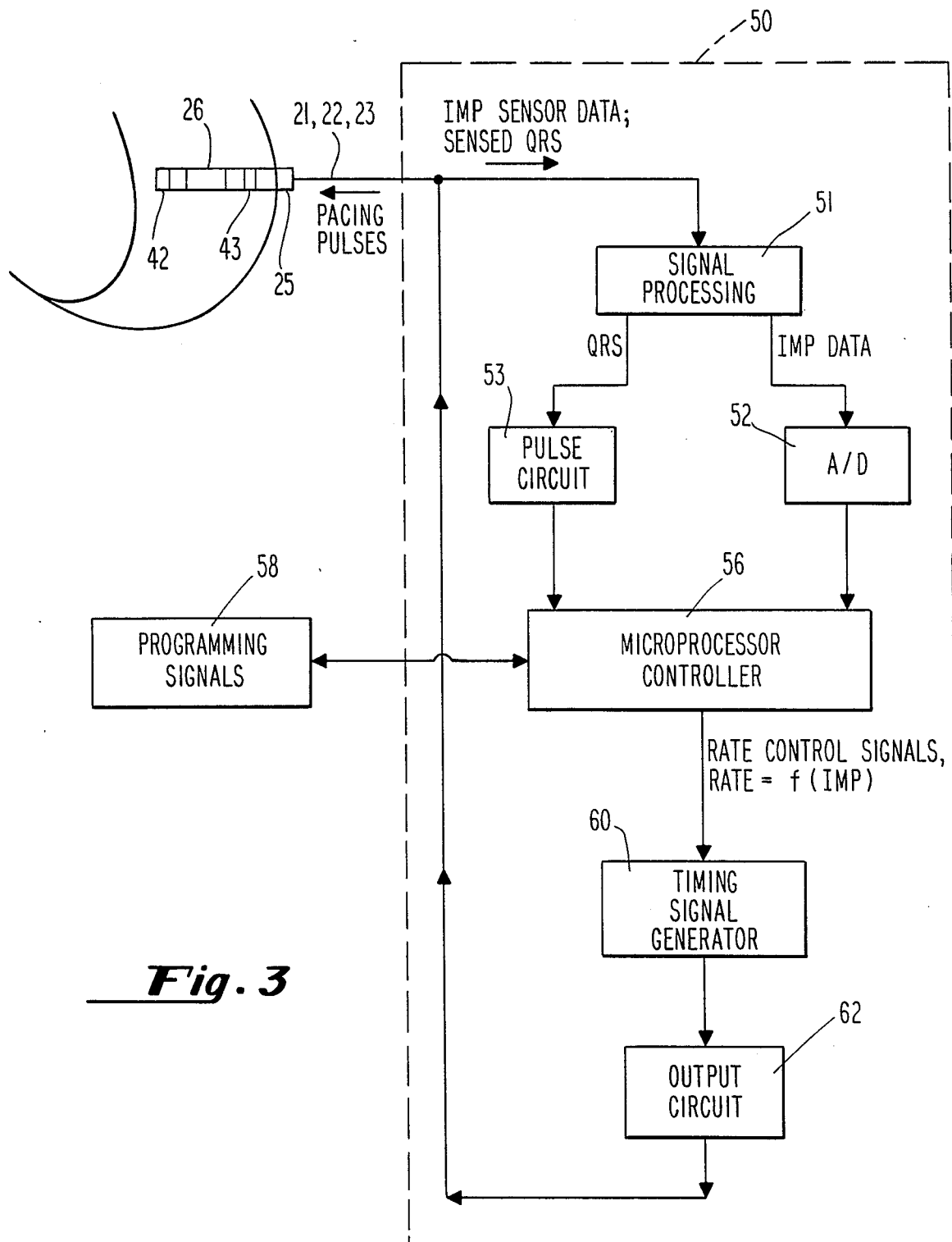
FIG. 3 is a block diagram showing the overall pacing system and method of this invention.

Referring now to FIG. 3 there is shown a schematic diagram illustrative of the pacing system and method of this invention. As illustrated, a pacemaker 50, suitably implanted in the patient, communicates with the lead tip 25 which is fixed in the myocardium, through electrical conductors 21, 22, 23. Pacemaker 50 is suitably a programmable pacemaker and can receive programming signals from an external source 58 of known design, and additionally can communicate information back out to the external apparatus 58. As illustrated, the pacemaker is preferably microprocessor controlled in order to provide optimum control, is known in the art. Suitable battery source means, not illustrated, provide power to the pacemaker.

Two inputs are received from the implanted lead tip, namely the IMP sensor data and the sensed QRS signal. These are inputted to signal processing circuit 51 of conventional design, which detects the inputs and provides clear signal outputs. For the IMP data, signal processing circuit 51 may suitably include a bridge-type configuration for measuring the impedance change of pressure sensor 26. The IMP data is outputted to an analog to digital converter 52, which converts the analog signal representative of IMP into a digital format suitable for subsequent digital processing. The detected analog QRS signal is inputted to pulse circuit 53, which provides a timing pulse output indicative of the occurrence of the QRS signal when a natural heart beat has indeed been detected. The output of pulse circuit 53 is likewise inputted to microprocessor control circuit 56.

Microprocessor controller 56 comprises the means, in hardware and/or software form, for carrying out the well known control functions performed in a modern demand pacemaker. Thus, the controller circuit 56 comprises a timing circuit for timing out a normal pulse stimulus rate, resetting the timing means upon the occurrence of a QRS, receiving programming signals from external apparatus 58, sensing battery life, etc. Controller 56 also preferably utilizes a microprocessor and associated memory which acts in cooperation with the required analog circuitry for performing controller functions. In the practice of this invention, a microprocessor is preferred for carrying out the algorithm which is used for determining pacing rate as a function of sensed IMP. The alogrithm may be software-controlled by instructions stored in RAM or ROM, or it may be carried out by conventional hardwired logic circuitry. In the preferred embodiment, the microprocessor and a portion of associated memory comprise logic means for carrying out the desired algorithm, e.g., a threshold seeking algorithm using a non-linear average process. Further, the associated memory may be re-programmed to change the algorithm, either by changing the mathematical step performed, or by changing constants which are used in calculating the relationship between sensed IMP and desired pacing rate. Further, the algorithm may use other sensed parameters, such as a detected pH or temperature in the heart muscle for modifying the rate determination. The output of the controller 56 containing information representative of the desired rate and the timing of pulse signals is connected to timing signal generator 60. Generator 60 produces a timing signal in response to the controller information, which timing signal is connected to output circuit 62. Output 62 responds to the timing signals by producing output pacing pulses of desired energy and form, which are connected to the pacing lead and hence to the electrodes 42, 43 at the lead tip.

Figure 4A:
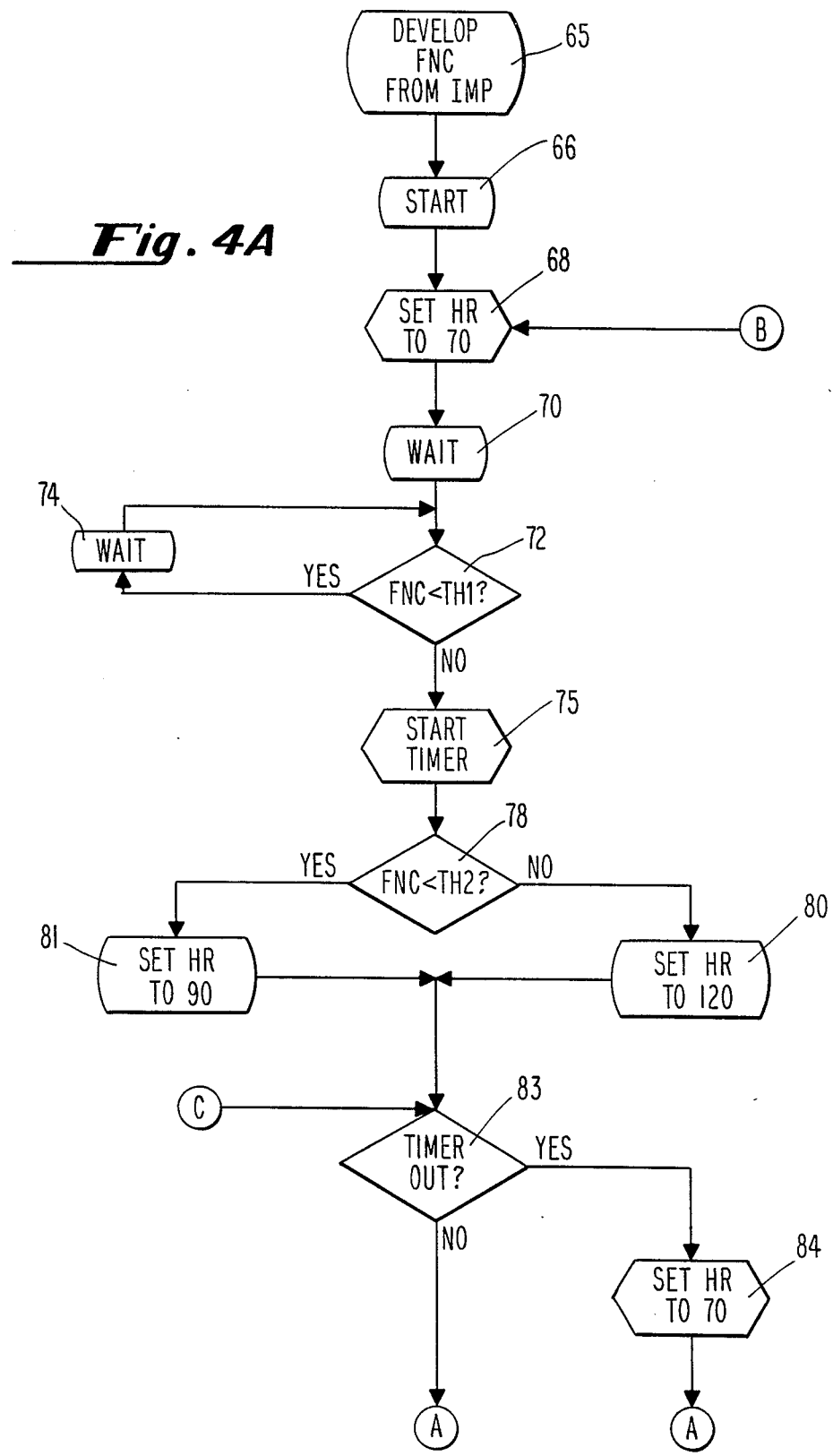
FIGS. 4A and 4B show an illustrative algorithm for use in the pacemaker and method of this invention.
Figure 4B:
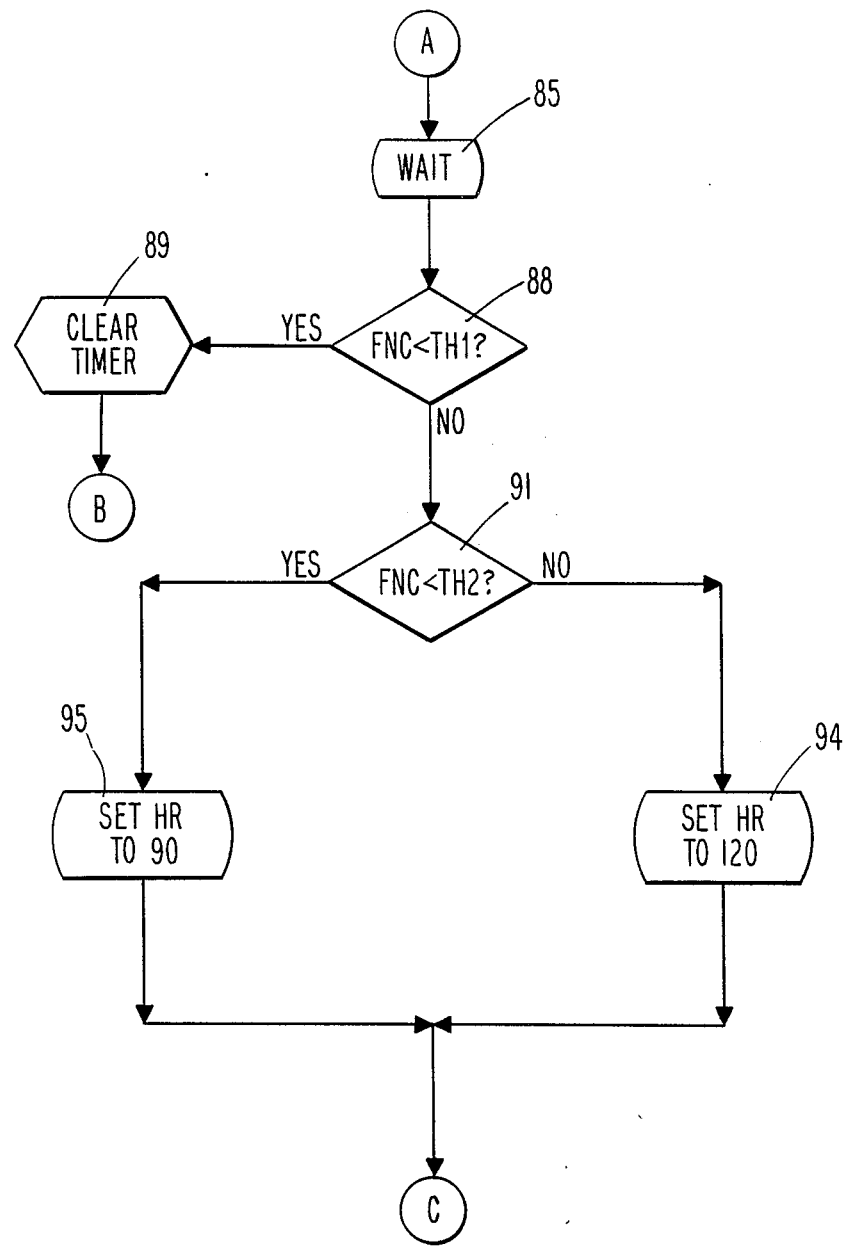
Figure 4C:
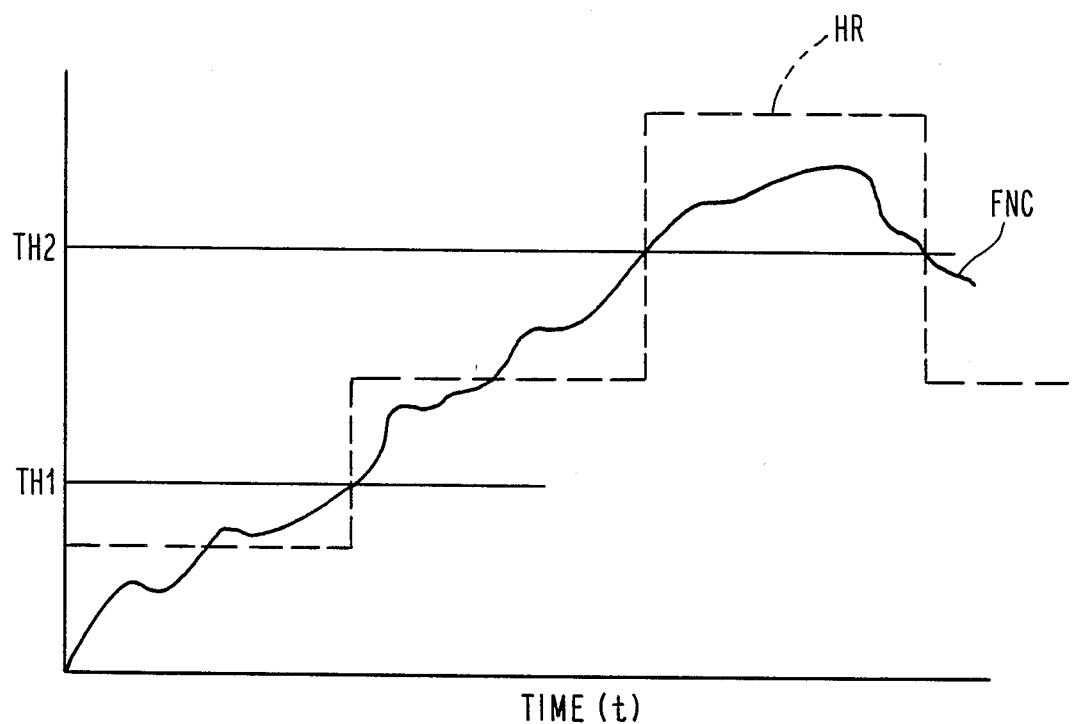
FIG. 4C illustrates changing heart rate as a function of IMP and the derived IMP function FNC(t).

Referring now to FIGS. 4A-4C, there is illustrated an algorithm for setting heart rate (HR) as a function of determined IMP. The preferred embodiment is illustrated as a software flowchart for use by a suitable microprocessor, as discussed above in connection with block 56 of FIG. 3. The system preferably incorporates a non-linear signal averaging means for processing the IMP signal. Specifically, a median average is obtained, followed by non-linear signal averaging. All data points around the median value and falling within a prescribed range are averaged together. This process results in relative noise immunity and prevents false trigger rates.

The algorithm continuously develops an IMP function FNC, as shown at 65. This algorithm may be operated, for example, every pacer cycle or after an accumulation of IMP data over a predetermined number of cycles. The IMP function FNC is preferably characterized by a regression analysis between the heart rate and intramyocardial pressure using both the peak value of IMP and the peak slope as parameters for controlling the heart rate and determining threshold levels (e.g., TH 1 and TH 2). FNC may also be made a function of one or more additional parameters measured by the lead or another sensor.

The algorithm for setting heart rate is started as indicated at 66. The algorithm may be started, or initiated, automatically during any pacer cycle, or it may be started only upon indication of change in IMP or FNC. The heart rate is intially set to 70 beats/minute (or any other desired basal rate) as seen at 68. The pacer then waits, at 70, for a convenient portion of the next pacer cycle. The function FNC(t) is compared to a preset threshold value TH1 at 72. This threshold value can be programmed externally to accomodate particular patient parameters. If the resultant function FNC(t) is less than the given threshold, the pacemaker remains at the preset heart rate, and waits at 74 for the next pacer cycle. If this condition is not satisfied, a timer is begun at 75. This timer can be programmed externally such that it does not allow the elevated heart rate to be maintained for more than 30 minutes or other desired time-interval. This represents a safety feature preventing a sustained high rate for periods well above a normal physiological response to stress.

The sequence continues at 78 where FNC is compared to another threshold level, identified as TH2. When this threshold level is satisfied, the algorithm branches at 80 where the heart rate is set to 120 beats/minute (which is a typical upper limit). If the given function is less than the TH2 level, the program branches at 81 where the heart rate is set at 90 (corresponding to the first level of heart rate change). Following this, at 83 the timer is checked, and if the given period has elapsed, the program goes to 84 and the pacemaker reverts automatically to the basal rate (in this particular example it is 70 beats/minute). If the time interval is not exhausted, the program continues directly to block 85 and waits for the next cycle. At 88, another check is made to see if the given function (FNC) is less than the first threshold level (TH1). If this condition is satisfied, the timer is cleared at 89 and the program returns to 68 where heart rate is set to 70. If the given function is not less than TH1, the program proceeds at 91 and goes through another check to see if FNC is less than TH2. If the resultant outcome is negative, heart rate is set to 120 at block 94; if the outcome state is positive, heart rate is set at 90 at block 95. At both blocks 94 and 95, the status of the current heart rate is checked and, if already at the indicated rate, the pacemaker is prevented from resetting. The program then goes back to 83 where the timer is checked, and the cycle is repeated again after waiting at 85.

FIG. 4C illustrates changes with time of function FNC(t), the two preset threshold levels, and the corresponding heart rate response shown as a dashed line. The algorithm is not restricted to only two rates beyond the basal rate, but in fact can be made to respond to multiple discrete rates or monotonically to the IMP-function changes with time. In addition, it is within the present invention to telemeter all of the measured values to external apparatus to allow optimal programmability of IMP-function parameters and guide sensor for maximal IMP-signal recording.

We claim:

1. A pacemaker system for rate-adaptive pacing of a patient, comprising:
   pulse means for generating pacing pulses;
   timing means for generating timing signals controlling the timing and rate of said pacing pulses, and connected to deliver said timing signals to said pulse means so as to control the rate of generated pacing pulses;
   lead means for delivering said pacing pulses to the heart of said patient, said lead means being connected to said pulse means and having electrode means for delivering said pacing pulses to said patient heart, said lead means also having sensing means for sensing patient heart beats and for generating heart signals representative thereof,
   myocardial contractile state means for generating signals representative of the myocardial contractile state of said patient's heart, said myocardial contractile state means comprising
   (a) intramyocardial pressure sensing means for sensing intramyocardial pressure within the heart wall and for generating signals representative of intramyocardial pressure, said intramyocardial pressure sensing means being positioned on said lead means for generating signals representative of intramyocardial pressure,
   (b) signal processing means connected to receive said intramyocardial pressure signals and for processing same, and
   (c) controller means connected to said signal processing means for generating contractility signals continuously representative of said myocardial contractile state and for determining a desired pacing rate as a function of said contractility signals,
   said controller means having an output connected to said timing means for controlling operation of same, whereby pacing pulses are delivered at a rate which corresponds to said patient contractile state.

2. The pacemaker system as described in claim 1, whrein said controller means comprises microprocessor means for receiving said signals from said signal processing means and for carrying out an alogrithm for determining said rate as a function of said received signals.

3. The pacemaker system as described in claim 2, wherein said signal processing means comprises analog to digital converting means for converting said intramyocardial pressure signals into digital signals for subsequent use by said controller means.

4. The pacemaker system as described in claim 1, wherein said controller means is programmable by externally supplied programming signals.

5. The pacemaker system as described in claim 1, wherein said lead means has a distal tip, said intramyocardial pressure sensing means and said electrode means being positioned in close proximity near said distal tip.

6. The pacemaker system as described in claim 5, wherein said signal processing means receives and processes said intramyocardial pressure signals on a cycle to cycle basis and said controller means generates said contractility signals continuously and controls said timing means cyclically as a function of said contractility signals.

7. The pacemaker system as described in claim 1, wherein said lead means comprises a screw-in fixation tip with an intramyocardial pressure sensor mounted thereon for engaging the heart myocardium when the tip is screwed into the myocardium.

8. The pacemaker system as described in claim 1, wherein said lead means comprises fixation means for fixing said intramyocardial pressure sensing means in the heart myocardium.

9. The pacemaker system as described in claim 1, wherein said intramyocardial pressure sensing means comprises a pressure sensor.

10. The pacemaker system as described in claim 1, wherein said lead means contains at about its tip additional sensing means for sensing at least one additional parameter associated with said patient's heart and for generating additional parameter signals representative of said additional parameter, said signal processing means being connected to receive and process said additional signals, and said controller means determines said pacing rate as a function of said additional parameter.

11. The pacemaker system as a described in claim 1, wherein said controller means comprises storage means for holding algorithm instructions for determining pacing rate as a function of patient intramyocardial pressure.

12. The pacemaker system as described in claim 11, comprising external programming apparatus for inputting alogrithm instructions into said controller means.

13. The pacemaker system as described in claim 12, wherein said external programming apparatus has means for inputting data into said controller means to cause said controller means to control pacing rate as a function of at least one other parameter.

14. The pacemaker system as described in claim 1, wherein said controller means has threshold means for comparing said contractility signals with at least one predetermined threshold during each cycle of a plurality of continuous pacing cycles, and wherein said controller means determines pacing rate as a function of said comparing.

15. The pacemaker system as described in claim 1, wherein said controller means comprises means for generating said contractility signals as a function of the peaks of the sensed intramyocardial pressure signals.

16. The pacemaker system as described in claim 1, wherein said controller means comprises means for generating said contractility signals as a function of the peak slopes of said intramyocardial pressure signals.

17. A demand pacing system having controllable means for generating pacing pulses on demand and lead means implantable in a patient's heart and connected to said controllable means for delivering said pacing pulses to said heart and for detecting the occurrence of natural heart beats in said heart, characterized by
   said lead means having sensor means for sensing within the patient myocardium a measure of patient myocardial contractility and for generating and delivering signals representative thereof to said controllable means, and
   said controllable means having rate control means for controlling the rate of said pacing pulses as a function of said representative signals.

18. The pacing system as described in claim 17, herein said sensor means comprises means for sensing intramyocardial pressure.

19. The pacing system as described in claim 17, wherein said rate control means controls said pacing rate at a selected one of a plurality of predetermined levels as a function of sensed myocardial contractility.

20. The pacing system as described in claim 17, wherein said lead means has further means for sensing at least one additional cardiac parameter, and said rate control means has means for controlling said rate as a function of said additional parameter.

21. The pacing system as described in claim 17, wherein said rate control means comprises algorithm means for determining pacing rate as a function of sensed myocardial contractility, and further comprises adjusting means for adjusting the determined pacing rate as a function of at least one other sensed cardiac parameter.

22. In a demand pacing system, a method of controlling the rate of delivered pacing pulses to a patient over a plurality of consecutive pacing cycles, comprising:
   sensing within the patient myocardium a measure of myocardial contractility of said patient's heart each of said pacing cycles, and
   determining desired pacing rate as a predetermined function of said sensed contractility and pacing said patient as a function of said determined rate.

23. The method as described in claim 22, comprising programming said pacemaker to perform said determining in accordance with a programmed algorithm.

24. The method as described in claim 23, comprising re-programming said algorithm from an external source.

25. The method as described in claim 23, comprising sensing at least one other cardiac parameter, and modifying said algorithm as a function of said sensed other parameter.

26. The method as described in claim 23, comprising normally pacing said patient at a base pacing rate, determining when said desired pacing rate is determined to be above said base rate, timing out a predetermined time whenever said desired pacing rate is determined to be above said said base rate, and adjusting the pacing rate back to said base rate after timing out said predetermined time.

27. The method as described in claim 22, wherein said sensing comprises generating a signal representative of intramyocardial pressure in the heart of said patient, and further comprising determining a measure of contractility each cycle as a function of said intramyocardial pressure.

28. The method as described in claim 22, wherein said sensing comprises sensing intramyocardial pressure and said determining comprises generating signals representative of the peak values of said sensed intramyocardial pressure.

29. The method as described in claim 22, wherein said sensing comprises sensing intramyocardial pressure and said determining comprises generating signals representative of the peak slopes of said sensed intramyocardial pressure.

30. The method as described in claim 22, wherein said sensing comprises sensing intramyocardial pressure and said determining comprises generating signals representative of at least one time dependent characteristic of sensed intramyocardial pressure during heart contraction.

* * * * *